United States Patent [19]

Shoemaker et al.

[11] Patent Number: 5,772,863
[45] Date of Patent: Jun. 30, 1998

[54] ELECTROCATALYTIC CERMET SENSOR

[75] Inventors: Erika L. Shoemaker; Michael C. Vogt, both of Westmont, Ill.

[73] Assignee: University of Chicago, Chicago, Ill.

[21] Appl. No.: 641,979

[22] Filed: May 1, 1996

[51] Int. Cl.[6] .................................................. G01N 27/407
[52] U.S. Cl. .......................... 204/426; 204/424; 205/784
[58] Field of Search .................................... 204/421–429

[56] References Cited

U.S. PATENT DOCUMENTS

| | | | |
|---|---|---|---|
| 2,965,842 | 12/1960 | Jacobson . | |
| 3,691,023 | 9/1972 | Ruka et al. | 205/784 |
| 3,860,498 | 1/1975 | Jones | 205/784 |
| 4,107,019 | 8/1978 | Takao et al. | 204/425 |
| 4,264,425 | 4/1981 | Kimura et al. | 204/412 |
| 4,300,991 | 11/1981 | Chiba et al. | 204/412 |
| 4,378,691 | 4/1983 | Terada et al. | 73/31.06 |
| 4,416,763 | 11/1983 | Fujishiro | 204/412 |
| 4,421,787 | 12/1983 | Ikezawa et al. | 204/421 |
| 4,462,890 | 7/1984 | Touda et al. | 204/426 |
| 5,352,344 | 10/1994 | Gohring et al. | 204/421 |
| 5,429,717 | 7/1995 | Vogt et al. | 205/779.5 |

*Primary Examiner*—T. Tung
*Attorney, Agent, or Firm*—Foley & Lardner; Michael D. Rechtin

[57] ABSTRACT

A sensor for $O_2$ and $CO_2$ gases. The gas sensor includes a plurality of layers driven by a cyclic voltage to generate a unique plot characteristic of the gas in contact with the sensor. The plurality of layers includes an alumina substrate, a reference electrode source of anions, a lower electrical reference electrode of Pt coupled to the reference source of anions, a solid electrolyte containing tungsten and coupled to the lower reference electrode, a buffer layer for preventing flow of Pt ions into the solid electrolyte and an upper catalytically active Pt electrode coupled to the buffer layer.

7 Claims, 12 Drawing Sheets

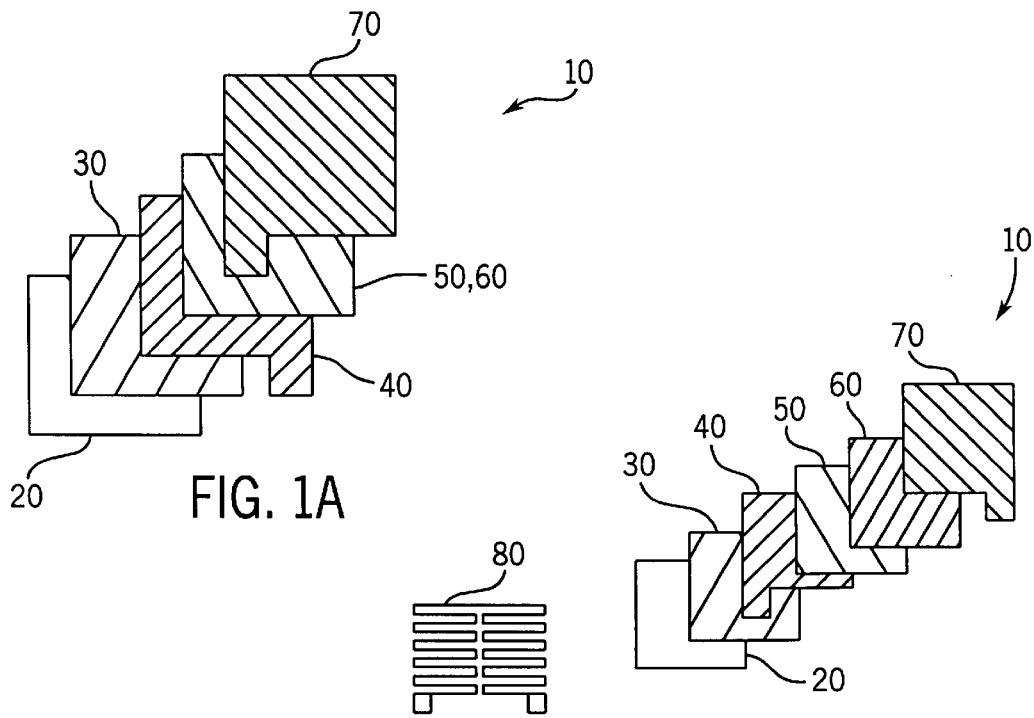
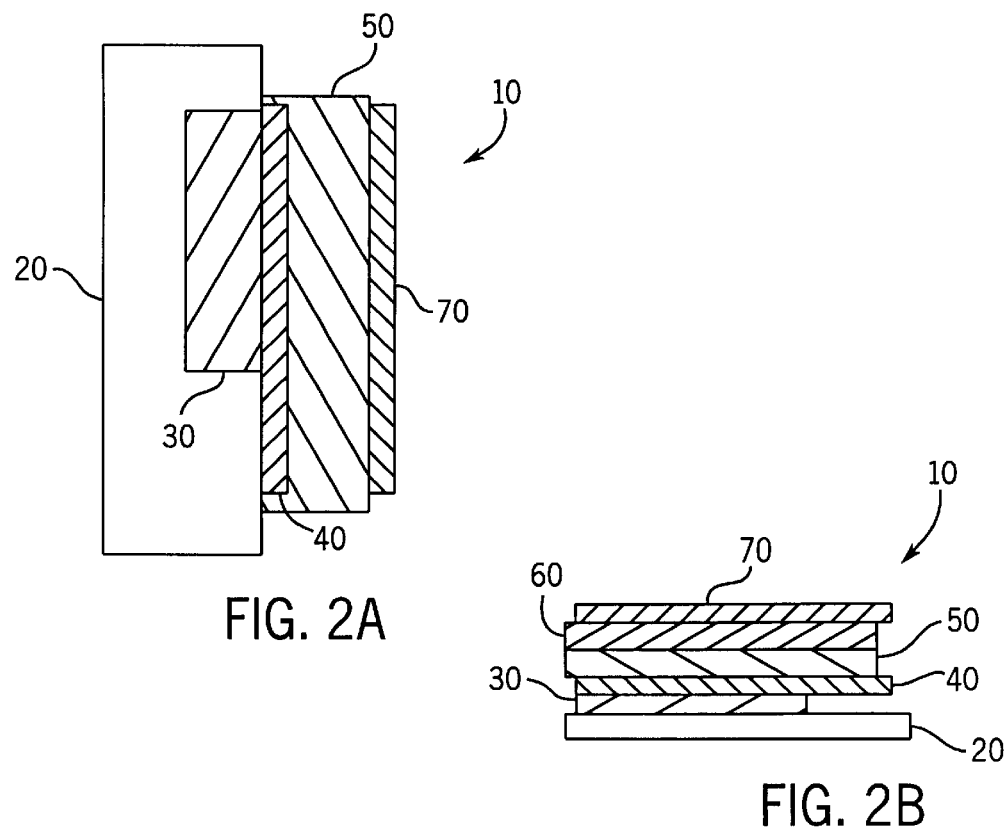

ELECTROCATALYTIC CERMET SENSOR

This invention was made with U.S. Government support under Contract No. W-31-109-ENG38 between the U.S. Department of Energy and the University of Chicago, and the U.S. Government has certain rights in this invention.

The present invention is concerned generally with an electrocatalytic cermet sensor. More particularly, the invention is concerned with a thick film cermet sensor employing cyclic application of voltage potentials to characterize oxygen and carbon dioxide present in a gas atmosphere. The sensor includes a plurality of device layers configured to enhance the sensitivity to $O_2$ and $CO_2$ gases.

Many needs exist in commercial industrial process control systems, particularly for the detection of $O_2$ and $CO_2$. Such applications include for example, automotive combustion systems, environmental monitoring systems, gas control systems and chemical processing equipment. Current methods typically utilize infrared spectroscopy and Fourier transform infrared analysis. Conventional gas sensors suffer from limited selectivity, substantial signal drift and limited range, signal saturation problems. In addition many industrial processing environment present harsh chemical conditions which often degrade and render inoperable conventional gas sensors.

It is therefore an object of the invention to provide an improved gas sensor for industrial processes and breathing apparatus.

It is another object of the invention to provide a novel method and system for sensing $O_2$ and $CO_2$ gases.

It is a further object of the invention to provide an improved thick film cermet sensor and method of detecting $O_2$ and $CO_2$ gases.

It is an additional object of the invention to provide a novel system and method for application of cyclic voltages for electrocatalytic detection of $O_2$ and $CO_2$ gases.

It is still another object of the invention to provide an improved method and system utilizing a refractory oxide based layer, solid electrolyte layer for providing enhanced sensitivity to $O_2$ and $CO_2$ gases.

It is yet a further object of the invention to provide a novel system and method for applying cyclic voltage to generate electrical output patterns characteristic of a particular gas, such as $O_2$, $CO_2$, CO, $N_2$ and various hydrocarbons.

The present invention includes a plurality of layers arranged to create a catalytically enhanced device for selected gases, such as $O_2$ and $CO_2$. In a preferred embodiment the sensor has five overlapping thick film layers on an aluminum oxide substrate with a Pt heating element in thermal contact with the aluminum oxide. Adjacent the alumina substrate is a reference electrode of a metal/metal oxide which provides a buffered electrode of low fixed oxygen activity. This reference electrode acts as a constant source of oxygen anions to a solid electrolyte layer with an intervening lower Pt electrode. The solid electrolyte layer is a tungsten stabilized bismuth oxide which permits the passage through the sensor exclusively of oxygen anions. A yttrium stabilized zirconia layer is disposed adjacent the tungsten stabilized bismuth oxide layer and acts as a buffer layer to prevent ions from the adjacent upper catalytic Pt electrode from diffusing into and through the tungsten stabilized bismuth oxide layer. The yttrium stabilized zirconia layer also provides an additional interface to promote $CO_2$ reactions. The upper and lower Pt electrodes mentioned hereinbefore also serve as catalytically active layers, as well as electrical parameter measurement electrodes. The device is operated by applying a cyclic voltage, such as a triangular potential, is ramped through the upper and lower Pt electrodes and absorbed $O_2$ and $CO_2$ react as follows:

$$O(ads)+2e^-=O^{2-}$$

$$CO_2(ads)-2e^-=CO(ads)+O^{2-}$$

As these reactions take place, the $O^{2-}$ ions generated pass through the tungsten stabilized bismuth oxide layer and are measured as a current by the gas sensor. The measured current is plotted against applied voltage to create a voltammogram, or characteristic pattern. The tungsten stabilized bismuth oxide layer and yttrium stabilized zirconia layer act to generate these unique patterns characteristic of $O_2$ and $CO_2$. The gas sensor temperature can also be varied to further enhance the unique pattern of the gases being monitored.

Without limiting the scope of the invention, it is believed the reactions of $O_2$ and $CO_2$ in the gas sensor are based on the same general response mechanism. Because the solid electrolyte of tungsten stabilized bismuth oxide is a conductor of $O_2$ ions, the overall response of the sensor primarily depends on the number of $O_2$ ions available at the solid electrolyte/electrode boundary. Therefore for $O_2$ detection the response mechanism involves direct supply of $O_2$ ions to the electrolyte/electrode boundary, and the change is measured as electronic current through the gas sensor across the solid electrolyte. In the case of $CO_2$ a catalytic reaction is believed to be necessary. The use of tungsten as part of a solid electrolyte layer substantially enhances the chemisorption of $CO_2$ and reaction in accordance with the equilibrium expression above.

These and other objects and advantages of the invention will be apparent from the detailed description and drawings described hereinbelow.

BRIEF DESCRIPTION OF THE DRAWINGS

FIG. 1A illustrates generally an exploded view of layers of an electrocatalytic sensor constructed in accordance with the invention and FIG. 1B illustrates in an exploded view all the detailed layers of the sensor;

FIG. 2A illustrates generally an enlarged side view of a thick film cermet gas sensor device of the invention and FIG. 2B illustrates in the side view all of the detailed layers of the sensor;

DETAILED DESCRIPTION OF PREFERRED EMBODIMENTS

Figure 3:
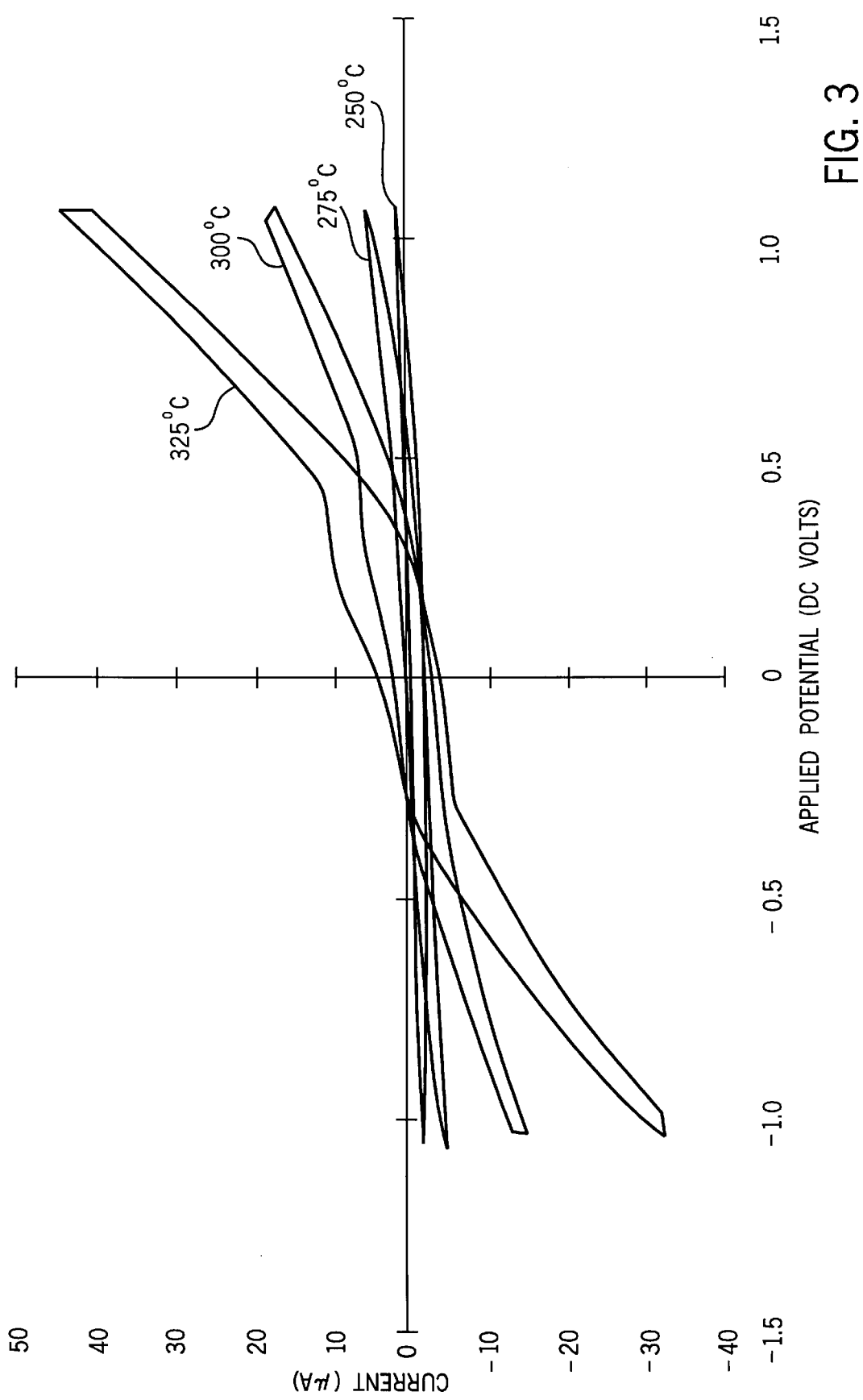
FIG. 3 illustrates a set of cyclic voltage outputs for $O_2$ gas for different gas sensor temperatures.

A gas sensor constructed in accordance with a preferred form of the invention is shown in FIGS. 1A, 1B, 2A and 2B, and indicated generally at 10. The gas sensor 10 includes an aluminum oxide substrate 20 with an adjacent metal oxide ion reference layer 30. This reference layer 30 acts to provide a constant source of oxygen ions in the gas sensor 10 and thus minimizes drift in response over time. This reference layer 30 acts to provide a constant source of oxygen ions in the gas sensor 10 and thus minimizes drift in device response over time. Most preferably the reference layer 30 is NiO, and details of preparation are described in Example 1. Above the reference layer 30 is a lower catalytic electrode 40 preferably made of Pt, and details of preparation are also described in Example 1. Above the lower catalytic electrode 40 is a first solid electrolyte layer 50, preferably composed of a plurality of layers of tungsten stabilized bismuth oxide and also included is a buffer layer 60 (such as, yttrium stabilized zirconia). This buffer layer 60 helps prevent diffusion of unwanted ionic species into the first electrolyte layer 50. Details of preparation of this combined layer are also set forth in Example 1. Above the first electrolyte layer 50 and the buffer layer 60 is an upper catalytic electrode 70, and details of preparation are further described in Example 1. In addition to the above described layers, it is also helpful to include a heating element layer 80, as shown in FIG. 1B, which can be disposed in thermal contact with the lower side of the aluminum oxide substrate 20. The ability to change temperature of the gas sensor 10 enhances the ability to generate characteristic patterns of selected gases in contact with the gas sensor 10. Further details of some of the layers and aspects of the gas sensor 10 and preparation of some of the layers are described in U.S. Pat. No. 5,429,727, which is incorporated by reference herein.

The gas sensor 10 was tested to illustrate its sensitivity to various example conditions. In Example 2 are explained the testing conditions and various test results set forth in Example 3 through 7 and illustrated in FIGS. 3–12. The resulting characteristic patterns can be analyzed by any conventional pattern recognition methodology, such as neural network formalisms and the like.

The following nonlimiting examples illustrate various aspects of gas sensor manufacture and gas sensing results.

EXAMPLE 1

The substrate for the gas sensor can be any electrically non-conductive material which is chemically stable at temperatures above 200° C. The substrate should also be impermeable to gas diffusion. Examples of such materials are ceramics including alumina, spinel, mullite, forsterite and others.

The reference ion source could be one of a number of nonstoichiometric metal oxides which could act as a reversible source of anions and provide a reliable source of ions to support continued reaction. Nonstoichiometric metal oxides such as nickel/nickel oxide (Ni/NiO) were particularly good ion sources since they provided a well-buffered source of oxygen ions in galvanic cells. The metal oxide combination provided an oxygen sink/source reservoir described by the equilibrium equation:

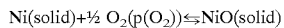

where $p(O_2)$ was the oxygen partial pressure. Equilibrium was achieved when $p(O_2)$ had penetrated the metal and oxide. Homogeneity of $p(O_2)$ was maintained at the electrode/electrolyte interface by O anion migration in the electrolyte, and electron activity in the metal phase of the Ni/NiO system. The electron activity reaction is described by:

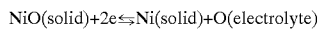

In the driven mode of operating the gas sensor (applying a cyclic voltage), the preferred metal oxide reference served as a constant oxygen ion source which stabilized the sensor response even in oxygen deficient environments. Suitable materials included, for example, CdO, ZnO, CaO, CoO, CuO, FeO, MnO, VO, TaO, CrO and NiO.

The lower electrode also preferably is a catalytic metal. In the presence of an applied voltage, the upper and lower electrodes both act as catalytic surfaces. The electrode polarity alternates with the reversing voltage, and suitable choices are Pt and Pd.

The solid electrolyte should preferably be a good conductor of oxygen anions. In addition, the solid electrolyte should be doped with a $WO_3$ to provide W lattice sites within the structure to promote $CO_2$ reactions. The material could be selected from among a variety of W doped ionically conductive electrolytes such as $WO_3$—$ZrO_2$, $WO_3$—$Bi_2O_3$. $WO_{2.78}Bi_2O_{2.22}$ was preferable due to its high O ion conductivity, low conductivity temperature and well-documented performance as an ionic conductor.

The upper electrode should be a catalytically active material which promoted the oxidation of gas species. Such materials include Pt, Ru and Pd.

The Pt paste used for the heating element and the upper/lower electrode construction was pre-fabricated oxygen sensor electrode paste from Heraeus Cermalloy (OS1). The paste was 85% solids, and 15% vehicle with a ground glass fit to aid film sintering and increase the porosity of the films after firing. The commercial Pt paste was thinned to 80 wt % (paste) and 20 wt % Heraeus Cermalloy RV-025 electronic vehicle (containing terpineol and ethyl cellulose).

The NiO metal oxide reference was made with Johnson Matthey spray-dried nickel oxide powder. The powder was pulverized to pass through a 325 mesh (lines per inch) filter and then mixed in a ratio of 24 wt % NiO to 76 wt % Heraeus Cermalloy RV-025 electronic vehicle to form a smooth paste.

The $YO_3$—$Zr_2O$ solid electrolyte used for the buffer layer was commercially purchased from Toyosoda in a composition of 8 ml % $YO_3$. The YSZ was pulverized to pass through a 325 mesh filter and then mixed in a ratio of 35 wt % YSZ and 65 wt % Heraeus Cermalloy RV-025 electronic vehicle to form a smooth paste.

The $WO_3$—$Bi_2O_3$ paste was fabricated as $WO_{3(O.22)}Bi_2O_{3(0.78)}$ powder using mixed oxide synthesis at Argonne. The powder was pulverized to pass through a 325 mesh filter and then mixed in a ratio of 35 wt % WBO and 65 wt % Heraeus Cermalloy RV-025 electronic vehicle to form a smooth paste.

A Presco™ Model 8025 industrial screen printer with an adjustable mounting table and built in video registration display was used to deposit the thick films. The printer could accurately place films within±125 µm. The printer screens consisted of stainless steel woven mesh stretched tightly over a frame with a stencil of light sensitive photographic emulsion adhered to the center. The screen was mounted on an automatic hydro-pneumatic press. A squeegee pressed paste through the mesh onto a mounted substrate at a constant rate and pressure. The screen patterns were made on 300 mesh, 45° oriented screens. The tension of the screens on their frame was measured at a 1 mm deflection for a 500 g load. The substrates were mounted 12 mm below the screens.

The substrates used were Coors ceramic aluminum oxide substrates that measured 12.7×12.7×0.3125 mm and were laser perforated into ten, separate substrates measuring 6.35×2.54×0.3125 mm. The pastes were screened onto the substrates and fired in the order represented by FIG. 1B.

1. The Pt heating element was screened first on the back of the $Al_2O_3$ substrate and fired at a controlled heating schedule to 1350° C. for 0.5 hr. The fired layer was 10 µm thick.

2. The Ni/NiO reference was screened as the first layer on the opposite side of the substrate from the heating element, and fired at a controlled heating schedule to 1350° C. for 0.5 hr. The fired layer diffused into the $Al_2O_3$ substrate forming a nickel aluminate spinel 3–4 µm thick.

3. The lower Pt electrode was screened over the metal oxide reference and fired at a controlled heating schedule to 1350° C. for 0.5 hr. The fired layer was 10 µm thick.

4. The $WO_3$—$Bi_2O_3$ solid electrolyte was screened in consecutive layers on top of the lower Pt electrode, and fired in between each layer at 850° C. for 1 hour. The YSZ buffer layer was screened in consecutive layers on top of the $WO_3$—$Bi_2O_3$ and fired in between each layer at 850° C. for 1 hr. The cumulative thickness of both the $WO_3$—$Bi_2O_3$ solid electrolyte, and the YSZ buffer layer was≈40 µm thick.

5. The upper Pt electrode was screened over the buffer layer and fired at a controlled heating schedule to 850° C. for 1 hr.

Figure 13:
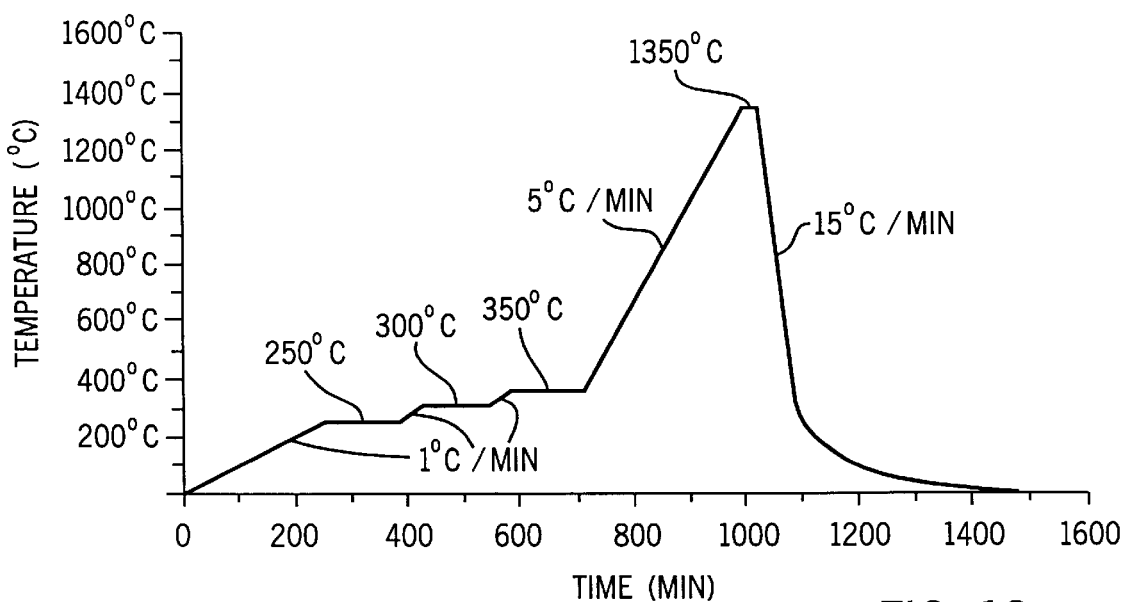
FIG. 13 illustrates the furnace firing schedule for preparation of the heating element, the reference ion source and lower reference electrode portion of the gas sensor.
Figure 14:
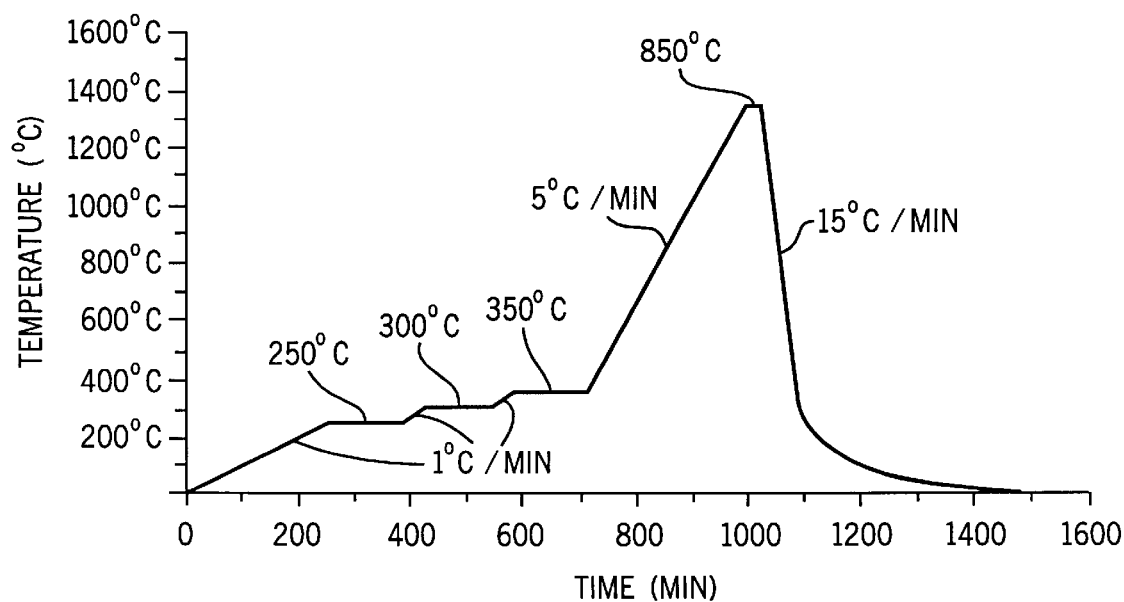
FIG. 14 illustrates the furnace firing schedule for preparation of the solid electrolyte layer, the buffer layer and upper catalytic electrode portion of the gas sensor.

The films were fired in a Lindberg Super Kanthal furnace controlled by a Eurotherm programmable controller. The firing schedules for the heating element, ion source, and lower reference electrode were implemented as shown in FIG. 13. The slow ramping up to 350° C. was used to keep the rate of out-gassing of the organic vehicle to a minimum to ensure smooth, uniform films. The firing schedules of the solid electrolyte, buffer layer and upper catalytic electrode were implemented according to the schedule in FIG. 14. The maximum temperature for firing the WBO materials to prevent melting was 850° C. The Pt, Ni/NiO, YSZ materials could be fired to 1350° C.

EXAMPLE 2

The chamber used for as testing was constructed from a 500 ml bell-type flask having a sealed spherical end and a 50 mm open end. The stopper that sealed the chamber was channeled, and two 8 mm stainless steel tubes were run through the channels as feed-throughs for the test and the measurement leads. A gap left in each feed-through allowed the incoming gas to escape so that a small positive pressure of the test gas in the chamber could be maintained, assuring that no ambient air intruded during a test. The sensor was held by a spring-loaded test clip with gold-plated fingers. A micro-mass K-type thermocouple was used to measure the surface temperature of the sensor.

Once the sensor reached the set-point operating temperature in the range of 200°–300° C., the input voltage was applied and the sensor sampled. Three, +1 to −1 VDC, 30 second long, triangular waveforms were applied to the gas sensor in succession, and the current passing through the gas sensor was sampled at approximately 100 points per waveform. These triple (3×100 points) voltage-current curves produced the voltammograms used in later analysis.

Gas standards of $O_2$, $CO_2$ and $O_2/CO_2$ mixtures in a balance of $N_2$ were introduced to the test chamber via a gas line manifold. A precision flowmeter was used to control the gas entering the chamber in two flushing stages. The first stage involved flushing the test chamber with approximately 50 chamber volumes at approximately 5 l/min. for 5 min. The second stage involved lowering the flow rate to 50 mil/min. to allow the sensor to equilibrate to the operating temperature. This flow rate was maintained during the sensor sampling.

The sensors were tested for drift over time by stabilizing them in air and allowing them to sit overnight. The sensors showed negligible draft with time.

Figure 5:
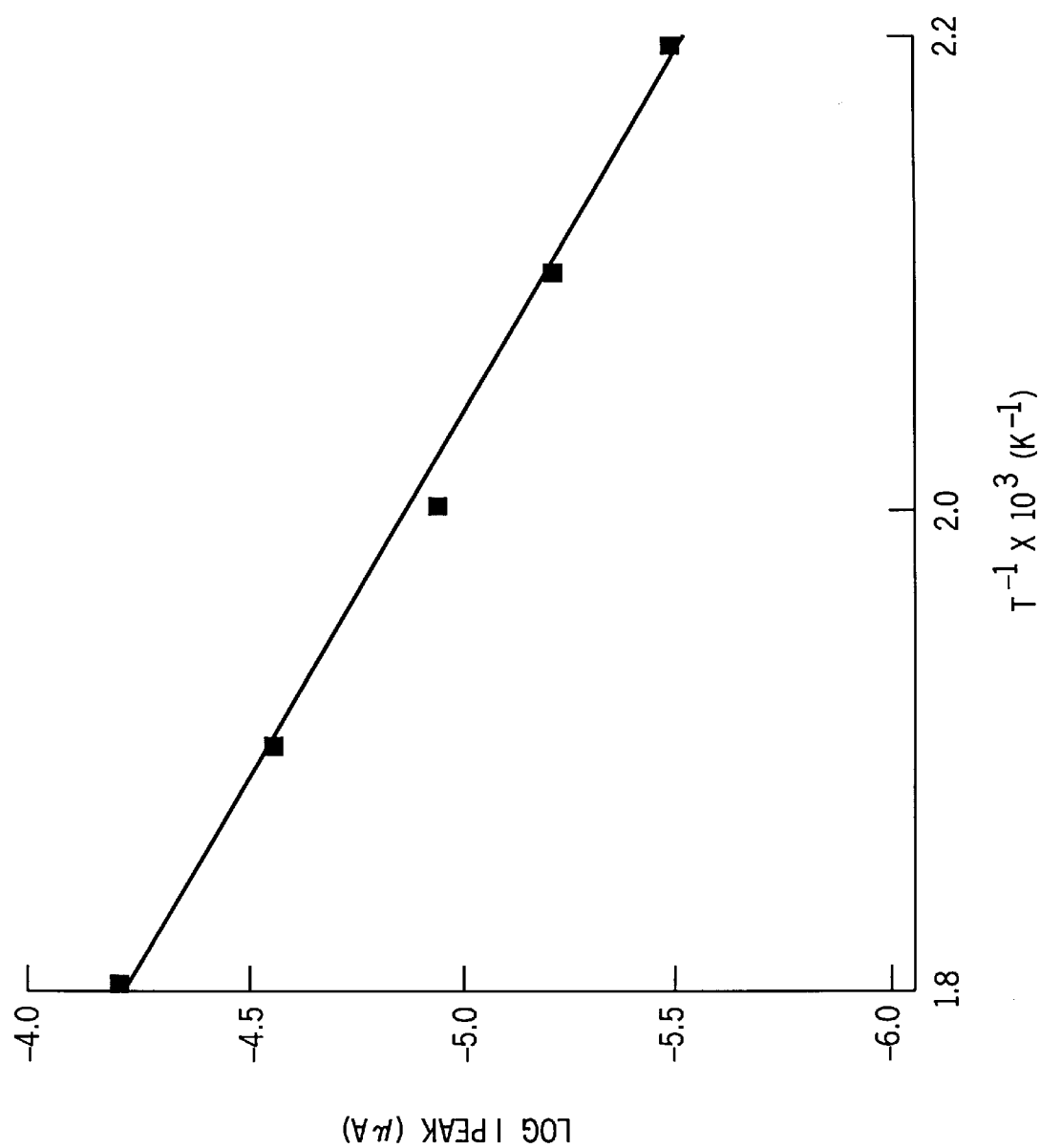
FIG. 5 illustrates a semilog plot of gas sensor current output versus the inverse of gas sensor temperature.
Figure 6:
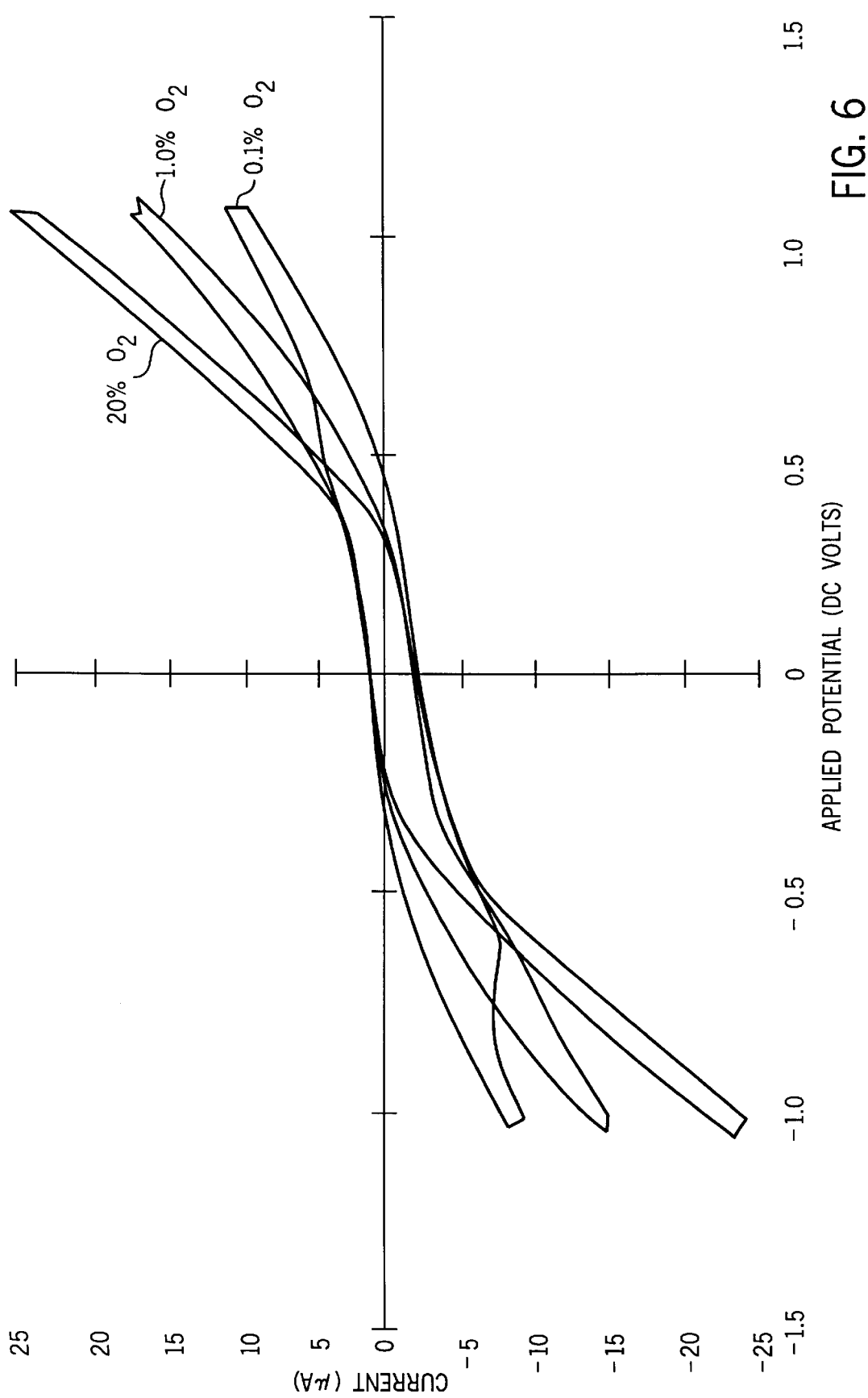
FIG. 6 illustrates a set of cyclic voltage outputs for various concentrations of $O_2$.

Two different sensors' responses to oxygen are illustrated by FIGS. 5 and 6. The gas sensors respond in the same way to changes in oxygen concentration.

EXAMPLE 3

The temperature dependence of the gas sensor was studied by stabilizing the gas sensor in air and increasing the temperature by 25° C. increments in the range of 175°–325° C. before sampling.

Figure 4:
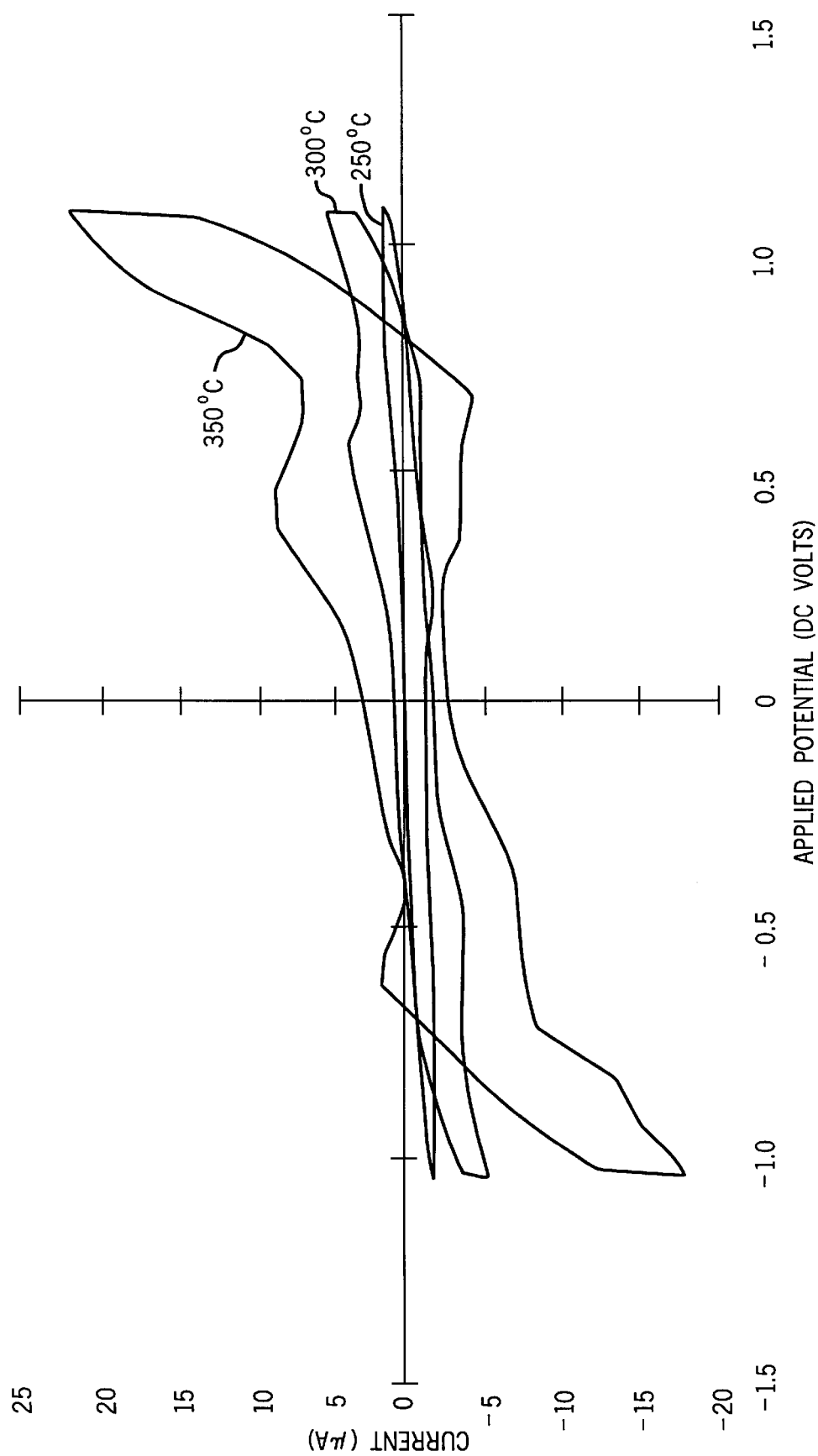
FIG. 4 illustrates a set of cyclic voltage outputs for CO as a function of gas sensor temperatures.

The dependence of the gas sensor was respect to change in temperature for $O_2$ and $CO_2$ are shown in FIGS. 3 and 4. For both gases, as temperature increases, the amplitude and sharpness of the peak current increase with the conductivity of the electrolyte. A plot of peak current vs. temperature shows a similar relationship to the typical conductivity dependence for an oxygen-ion-conducting solid-electrolyte (FIG. 5). The conducting range for the driven solid-electrolyte $Bi_2O_3$ cell is at much lower temperatures (200°–350° C.), as compared to a typical non-driven $Bi_2O_3$ solid electrolyte (500°–1100° C.). The lower temperature range is possible because of the presence of the applied voltage, which forces the ions through the electrolyte, as opposed to a strictly diffusion-controlled processing the non-driven cell.

EXAMPLE 4

The sensor response to oxygen is represented by the voltammograms in FIG. 6. Peaks on both the anodic and cathodic side increase with oxygen concentration. Since the sensor response is directly related to the amount of oxygen available at the tpb, this type of response was expected as the higher oxygen concentration directly supplied more oxygen for transport through the $WO_3$—$Bi_2O_3$ solid electrolyte.

EXAMPLE 5

Figure 7:
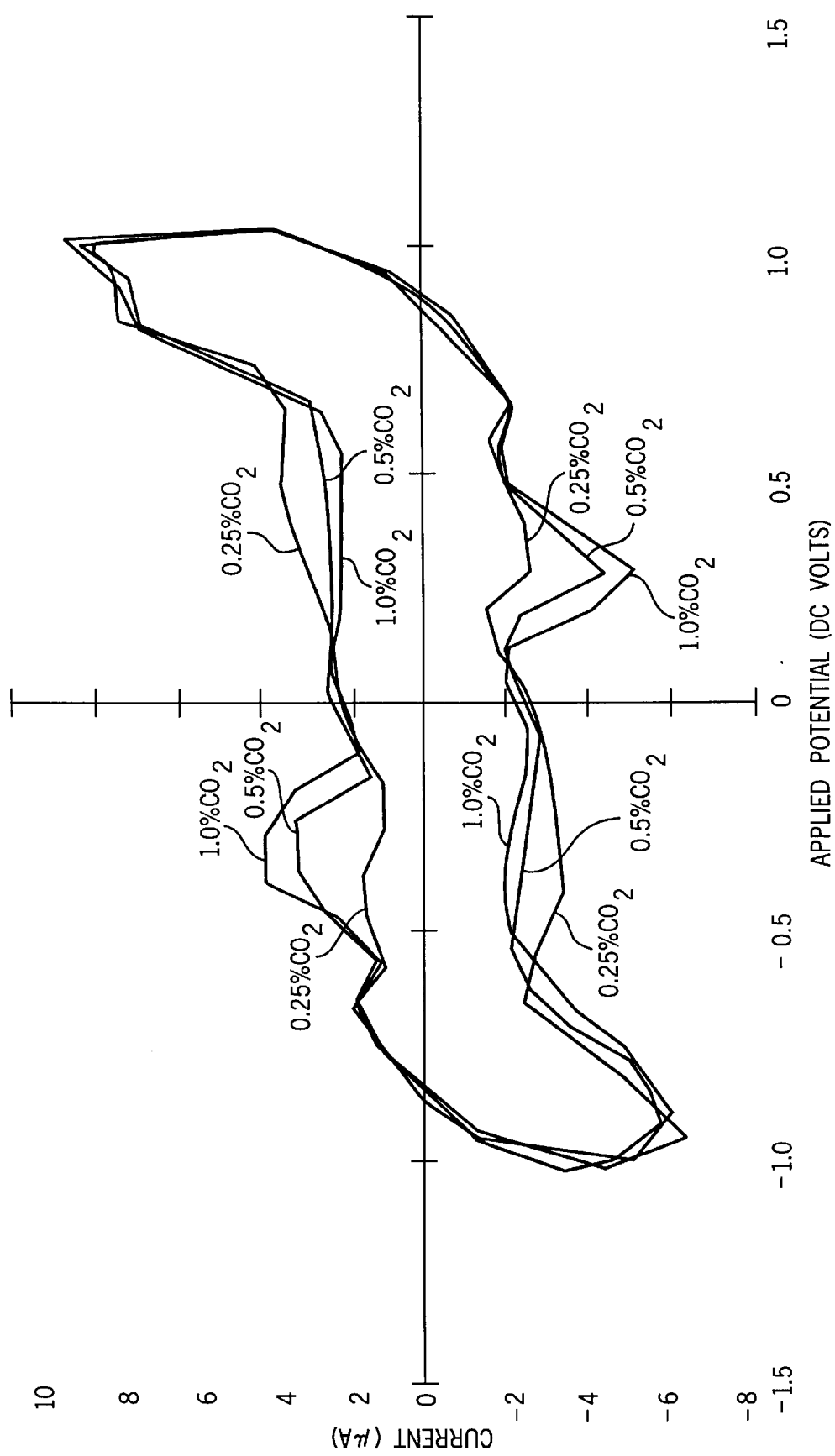
FIG. 7 illustrates a set of cyclic voltage outputs for various $CO_2$ concentrations.
Figure 8:
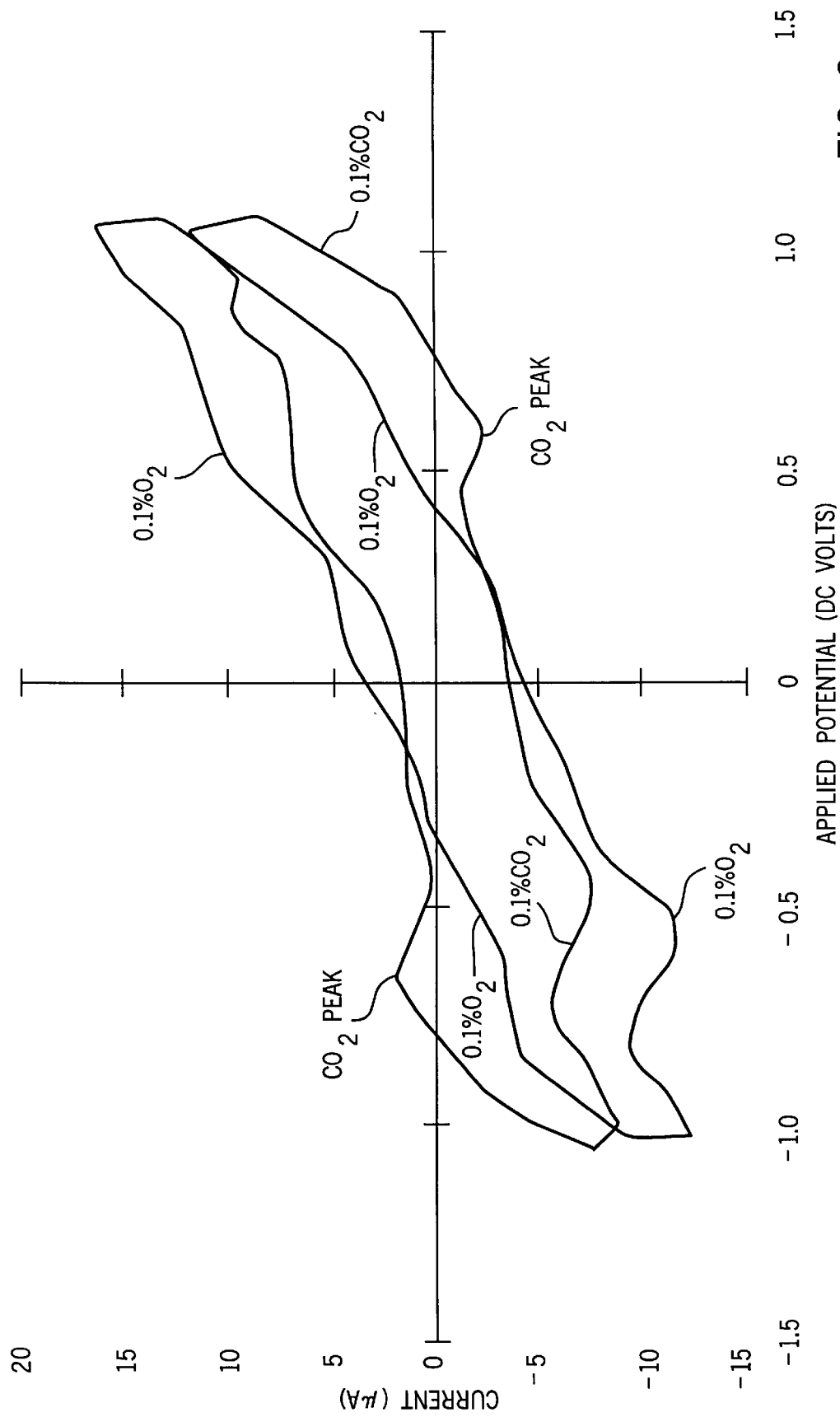
FIG. 8 illustrates a set of cyclic voltage outputs comparing $O_2$ and $CO_2$ responses for the same concentration by the gas sensor device of the invention.

FIG. 7 shows sensor response to various concentrations of carbon dioxide in a balance of nitrogen. As expected, the voltammogram for $CO_2$ in $N_2$ is significantly different than that of $O_2$ in $N_2$. A unique $CO_2$ peak is formed that increases with concentration (see FIG. 8). This response implies catalytic $CO_2$ reactions are occurring with a subsequent increase in ionic current through the bismuth oxide solid electrolyte.

EXAMPLE 6

Figure 9:
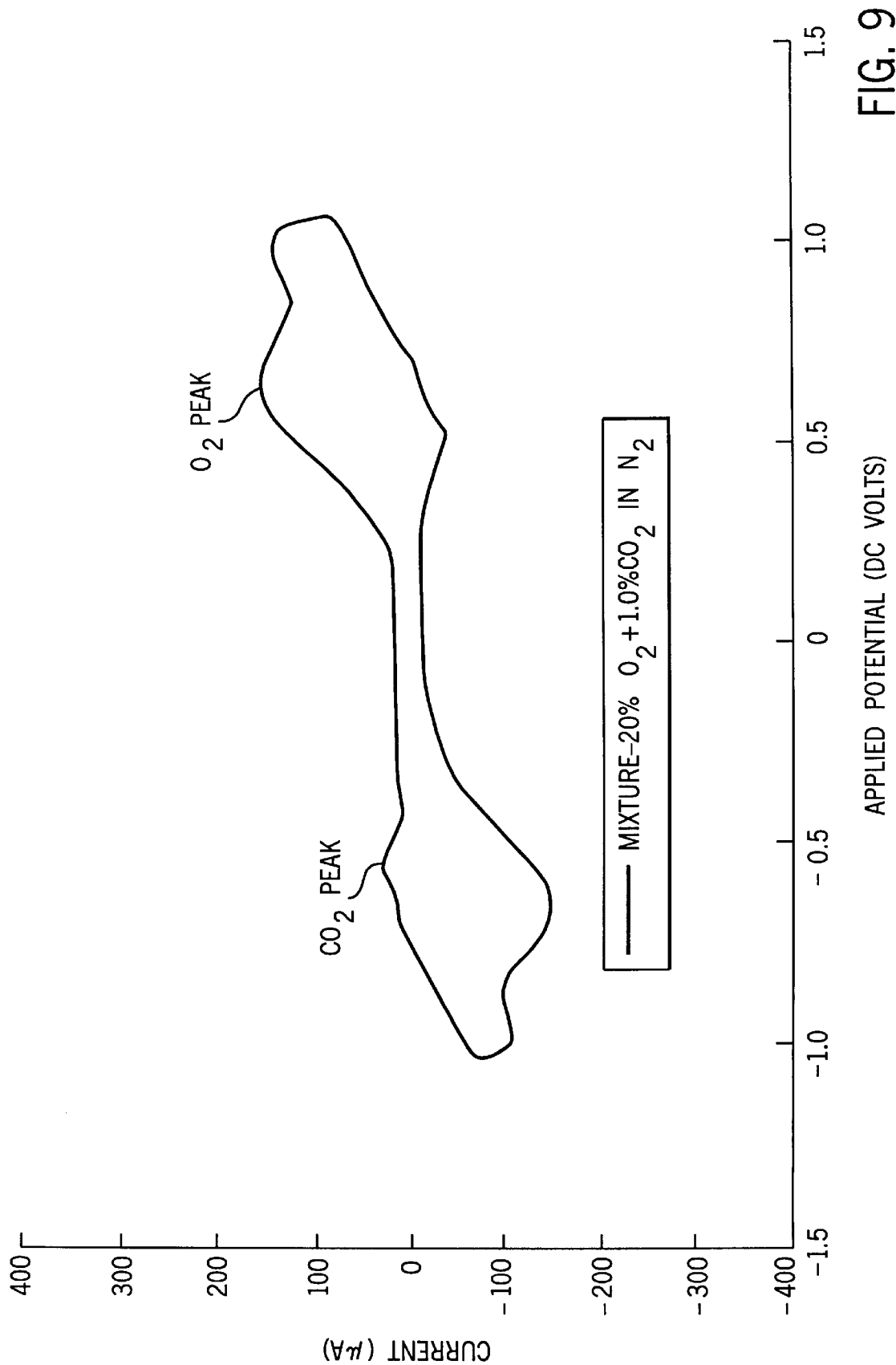
FIG. 9 illustrates a cyclic voltage output of the gas sensor for a $CO_2/O_2$ gas mixture.
Figure 10:
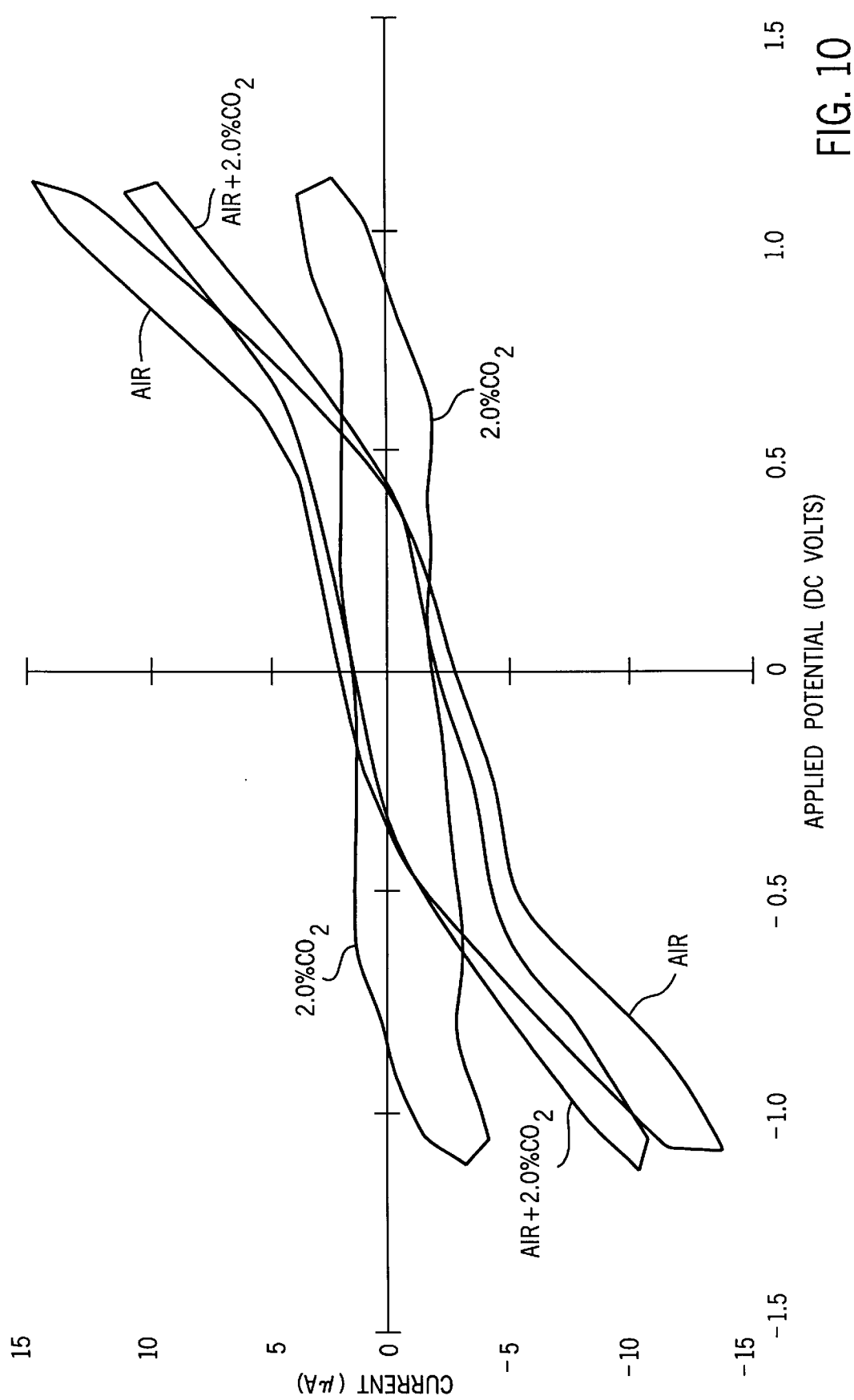
FIG. 10 illustrates a set of cyclic voltage outputs of the gas sensor for various mixtures of air and $CO_2$.

FIG. 9 shows the sensor response to a mixture of 1.0% $CO_2$ and 20% $O_2$. The voltammogram exhibits unique features from each gas. This response demonstrates potential to distinguish $O_2$ from $CO_2$ in mixtures. Larger concentrations of $CO_2$ in the mixture, however, confounds the response. The resulting voltammogram no longer exhibits distinctive features of the gases separately (see FIG. 10).

EXAMPLE 7

The effect of humidity was studied in both $O_2$ and $CO_2$ separately. The sensors were stabilized in each gas, while the humidity in the chamber was incrementally changed from 2% to 75%. To generate the desired humidities, saturated humectant salts were placed in the bottom of the spherical test chamber and stabilized at 20° C. with a constant temperature bath. The sensors were introduced into the chamber and allowed to equilibrate for 15 minutes before testing. A calibrated %RH meter was used to verify the humidity in the chamber. A table of the solutions used with their corresponding generated humidities is shown in Table 1. The sensors were tested first in bottled dry air before being introduced to the humidity chamber.

TABLE 1

Humectant Solutions

| Solution | Humidity @ 20° C. |
|---|---|
| Dry Air | 2% RH |
| Magnesium Chloride ($MgCl_2$) | 20% RH |
| Potassium Iodide (Kl) | 55% RH |
| Water Solution | 75% RH |

Figure 11:
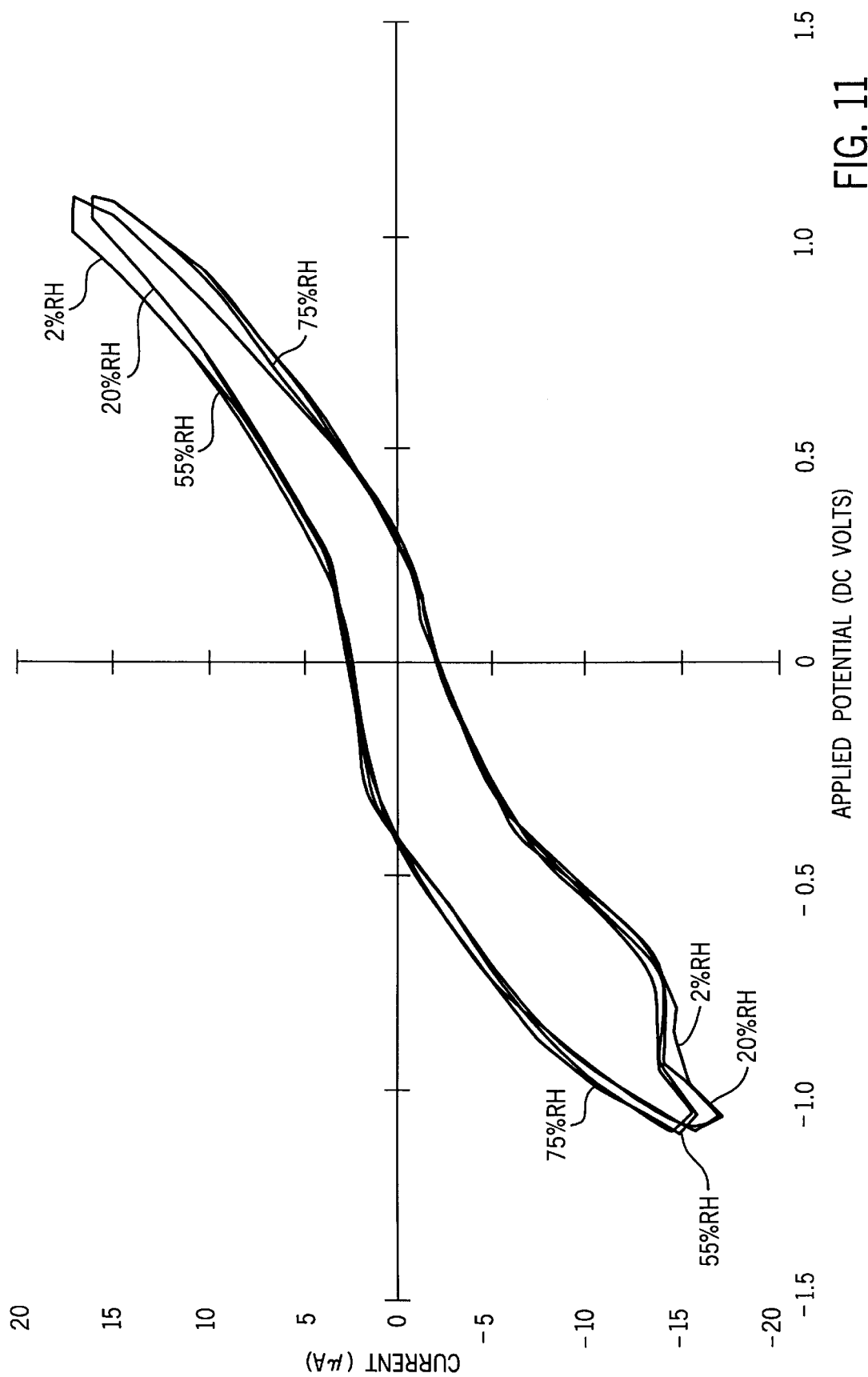
FIG. 11 illustrates a set of cyclic voltage outputs for $O_2$ with variable humidity levels.
Figure 12:
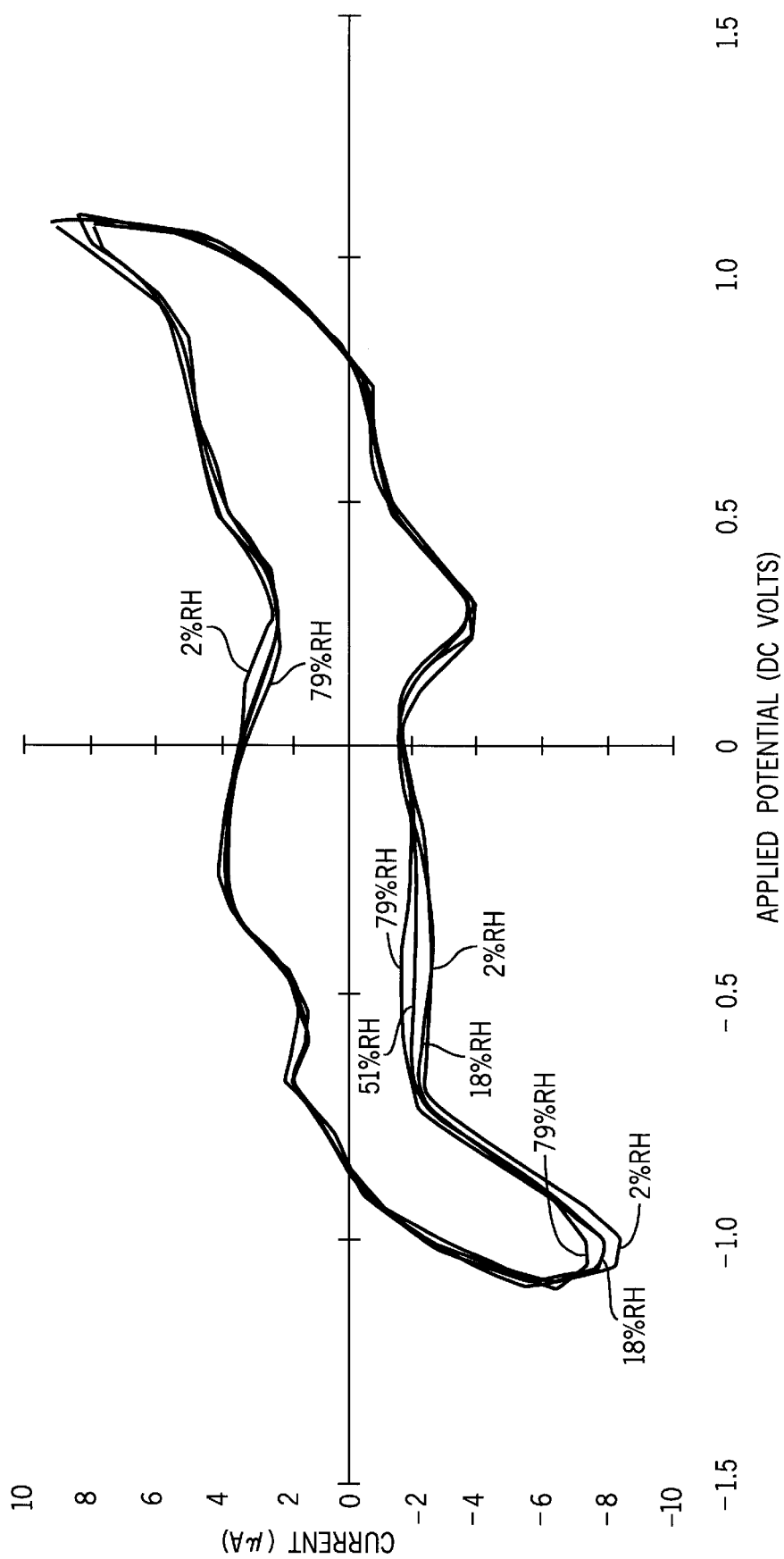
FIG. 12 illustrates a set of cyclic voltage outputs of the gas sensor for $CO_2$ with variable humidity levels.

Change in humidity had an insignificant effect on the sensors response to $O_2$ and $CO_2$ as shown in FIGS. 11 and 12. This result was expected. Since the surface of the sensor is heated to 200°–300°, no water vapor can condense on the electrodes to confuse the response.

While preferred embodiments of the invention have been shown and described, it will be clear to those skilled in the art that various changes and modifications can be made without departing from the invention in its broader aspects as set forth in the aforementioned claims.

What is claimed is:

1. A gas sensor for sensing $CO_2$, comprising:

a substrate layer;

a reference electrode source of oxygen anions and in electrical contact with said substrate layer, said reference electrode source of oxygen anions comprised of a nonstoichiometric compound enabling diffusion of oxygen anions therethrough;

a lower electrical reference electrode coupled to said reference electrode source of anions;

a solid electrolyte coupled to said lower reference electrode and consisting essentially of a tungsten-bismuth oxide to promote $CO_2$ reactions;

a buffer layer for preventing flow of Pt ions into said solid electrolyte; and an upper catalytically active electrode coupled to said buffer layer.

2. The gas sensor as defined in claim 1 wherein said tungsten-bismuth oxide is select from the group consisting of $WO_3$—$Bi_2O_3$ and $WO_{2.78}$—$Bi_2O_{2.22}$.

3. The gas sensor as defined in claim 1 wherein said reference electrode wource of anions is selected from the group consisting of Ni/NiO, Cd/CdO, Zn/ZnO, Ca/CaO, Co/CoO, Cu/CuO, Fe/FeO, V/VO, Ta/TaO, Cr/CrO and mixtures thereof.

4. The gas sensor as defined in claim 1 wherein said reference electrode of oxygen anions consists essentially of a cation rich binary compound.

5. The gas sensor as defined in claim 1 wherein said lower electrical reference electrode is selected from the group consisting of Pt, Cu, Ag and Pd.

6. The gas sensor as defined in claim 1 wherein said buffer layer comprises yttria stabilized zirconia.

7. The gas sensor as defined in claim 1 wherein said upper catalytically active electrode is selected from the group consisting of Pt, Ru, Rh, Os, Ir, Pd and Au.

* * * * *